US011002727B2

(12) United States Patent
Lavik et al.

(10) Patent No.: US 11,002,727 B2
(45) Date of Patent: May 11, 2021

(54) SCREEN PRINTING TISSUE MODELS

(71) Applicants: University of Maryland, Baltimore County, Baltimore, MD (US); UNIVERSITY OF MARYLAND, BALTIMORE, Baltimore, MD (US)

(72) Inventors: Erin Lavik, Ellicott City, MD (US); Steve Bernstein, Chevy Chase, MD (US); Adam Day, Frederick, MD (US); Bryan Ibarra, Miami, FL (US)

(73) Assignees: UNIVERSITY OF MARYLAND, BALTIMORE COUNTY, Baltimore, MD (US); UNIVERSITY OF MARYLAND, BALTIMORE, Baltimore, MD (US)

(*) Notice: Subject to any disclaimer, the term of this patent is extended or adjusted under 35 U.S.C. 154(b) by 81 days.

(21) Appl. No.: 16/047,707

(22) Filed: Jul. 27, 2018

(65) Prior Publication Data
US 2019/0187128 A1 Jun. 20, 2019

Related U.S. Application Data

(60) Provisional application No. 62/599,977, filed on Dec. 18, 2017.

(51) Int. Cl.
*G01N 33/50* (2006.01)
*C12N 5/00* (2006.01)
*B41M 3/06* (2006.01)
*B33Y 80/00* (2015.01)
*G09B 23/30* (2006.01)
*C12N 5/071* (2010.01)
*C12N 5/0793* (2010.01)

(52) U.S. Cl.
CPC .......... *G01N 33/5008* (2013.01); *B33Y 80/00* (2014.12); *B41M 3/06* (2013.01); *C12N 5/0062* (2013.01); *C12N 5/062* (2013.01); *C12N 5/0619* (2013.01); *C12N 5/0679* (2013.01); *G09B 23/30* (2013.01); *C12N 2513/00* (2013.01); *C12N 2533/32* (2013.01); *C12N 2533/52* (2013.01); *C12N 2533/54* (2013.01); *C12N 2535/00* (2013.01)

(58) Field of Classification Search
CPC .............. C12N 5/0062; C12N 2513/00; G01N 33/5008; B33Y 80/00; B41M 3/06; G09B 23/30
See application file for complete search history.

(56) References Cited

U.S. PATENT DOCUMENTS

2006/0136182 A1* 6/2006 Vacanti ................. G16H 50/50 703/11

OTHER PUBLICATIONS

Folch et al. "Microfabricated elastomeric stencils for micropatterning cell cultures" (2000) Journal of Biomedical Materials Research, vol. 52, No. 2: 346-353. (Year: 2000).*
Zhao et al. "Hierarchical PEG-Based 3D Patterns Grafting from Polymer Substrate by Surface Initiated Visible Light Photolithography" (2016) Macromolecular Rapid Communications, vol. 37: 1611-1617. (Year: 2016).*
Lin et al. "Application of visible light-based projection stereolithography for live cell-scaffold fabrication with designed architecture" (2013) Biomaterials, vol. 34: 331-339. (Year: 2013).*
Slaughter et al. "Hydrogels in Regenerative Medicine" (2009), Advanced Materials, vol. 21, Nos. 32-33: 3307-3329. (Year: 2009).*
Moon et al. "Spatial Control of Bacteria Using Screen Printing", 2016, 3D Printing and Additive Manufacturing, vol. 3, No. 4: 195-203 (Year: 2016).*
Ahmado, A., Carr, A. J., Vugler, A. A., Semo, M., Gias, C., Lawrence, J. M., Coffey, P. J. (2011). Induction of differentiation by pyruvate and DMEM in the human retinal pigment epithelium cell line ARPE-19. Invest Ophthalmol Vis Sci, 52(10), 7148-7159. doi:10.1167/iovs.10-6374.
Al Gwairi, 0., Thach, L., Zheng, W., Osman, N., Little, P. J. (2016). Cellular and Molecular Pathology of Age-Related Macular Degeneration: Potential Role for Proteoglycans. J Ophthalmol, doi:10.1155/2016/2913612.
Araki, K., Ogata, T. (1995). Three-dimensional configuration of crypts of different types of colorectal adenomas. Scanning Microsc, 9(1): 149-56. Abstract Only.
Barres, B. A., Silverstein, B. E., Corey, D. P., Chun, L. L. (1988). Immunological, morphological, and electrophysiological variation among retinal ganglion cells purified by panning. Neuron, 1(9), 791-803.
Booij, J. C., Baas, D. C., Beisekeeva, J., Gorge's, T. G., Bergen, A. A. (2010). The dynamic nature of Bruch's membrane. Prog Retin Eye Res, 29(1), 1-18. doi:10.1016/j.preteyeres.2009.08.003.
Brandl, C., Zimmermann, S. J., Milenkovic, V. M., Rosendahl, S. M., Grassmann, F., Milenkovic, A., Weber, B. H. (2014). In-depth characterisation of Retinal Pigment Epithelium (RPE) cells derived from human induced pluripotent stem cells (hiPSC). Neuromolecular Med, 16(3), 551-564. doi:10.1007/s12017-014-8308-8.
Canavan, C., West, J., Card, T. (2014). The epidemiology of irritable bowel syndrome. Clin Epidemiol, 6, 71-80.
Choi, S.H., et al. (2014). A three-dimensional human neural cell culture model of Alzheimer's disease. Nature, 515 (7526), 274-8.
Dubbin, K., Hori, Y., Lewis, K. K., Heilshorn, S. C. (2016). Dual-Stage Crosslinking of a Gel-Phase Bioink Improves Cell Viability and Homogeneity for 3D Bioprinting. Adv Healthc Mater. doi:10.1002/adhm.201600636.
Faulkner-Jones, A., et al. (2015). Bioprinting of human pluripotent stem cells and their directed differentiation into hepatocyte-like cells for the generation of mini-livers in 3D. Biofabrication, 7(4), 044102.

(Continued)

*Primary Examiner* — Teresa E Knight
(74) *Attorney, Agent, or Firm* — Tristan A. Fuierer; Olive Law Group, PLLC

(57) ABSTRACT

A process of simply, cheaply, and reproducibly creating complex tissue models using screen printing and the tissue model prepared using the screen printing process. These models are amenable to high throughput screening. They will allow the study of components of disease progression and can be used for screening therapies.

16 Claims, 6 Drawing Sheets

(56) References Cited

OTHER PUBLICATIONS

Fernandez-Godino, R., Pierce, E. A., Garland, D. L (2016). Extracellular Matrix Alterations and Deposit Formation in AMD. Adv Exp Med Biol, 854, 53-58. doi:10.1007/978-3-319-17121-0_8. Abstract Only.

Ford, M. C., Bertram, J. P., Hynes, S. R., Michaud, M., Li, Q., Young, M., Lavik, E. B. (2006). A macroporous hydrogel for the coculture of neural progenitor and endothelial cells to form functional vascular networks in vivo. Proc Natl Acad Sci U S A, 103(8), 2512-2517. doi:10.1073/pnas.0506020102.

Gu, Q., et al. (2016). Stem Cell Bioprinting: Functional 3D Neural Mini-Tissues from Printed Gel-Based Bioink and Human Neural Stem Cells. Adv Healthcare Mater, 5(12), p. 1428. Abstract Only.

Gu, Y., et al., (2012). The influence of substrate stiffness on the behavior and functions of Schwann cells in culture. Biomaterials, 33(28), 6672-81.

Hertz, J., Robinson, R., Valenzuela, D. A., Lavik, E. B., Goldberg, J. L. (2013). A tunable synthetic hydrogel system for culture of retinal ganglion cells and amacrine cells. Acta Biomater, 9(8), 7622-7629. doi:10.1016/j.actbio.2013.04.048.

Hollyfield, J. G., Bonilha, V. L., Rayborn, M. E., Yang, X., Shadrach, K. G., Lu, L., Perez, V. L. (2008). Oxidative damage-induced inflammation initiates age-related macular degeneration. Nat Med, 14(2), 194-198.

Hynes, S. R., Lavik, E. B. (2010). A tissue-engineered approach towards retinal repair: scaffolds for cell transplantation to the subretinal space. Graefes Arch Clin Exp Ophthalmol, 248(6), 763-778. doi:10.1007/s00417-009-1263-7.

Hyun, W. J., Lim, S., Ahn, B. Y., Lewis, J. A., Frisbie, C. D., Francis, L. F. (2015). Screen Printing of Highly Loaded Silver Inks on Plastic Substrates Using Silicon Stencils. ACS Appl Mater Interfaces, 7(23), 12619-12624. doi:10.1021/acsami.5b02487.

Jeong, C.G., et al. (2014). Screening of hyaluronic acid-poly(ethylene glycol) composite hydrogels to support intervertebral disc cell biosynthesis using artificial neural network analysis. Acta Biomater, 10(8): 3421-30.

Jin, R., Moreira Teixeira, L. S., Krouwels, A., Dijkstra, P. J., van Blitterswijk, C. A., Karperien, M., Feijen, J. (2010). Synthesis and characterization of hyaluronic acid-poly(ethylene glycol) hydrogels via Michael addition: An injectable biomaterial for cartilage repair. Acta Biomater, 6(6), 1968-1977. doi:10.1016/j.actbio.2009.12.024.

Kadimisetty, K., et al. (2016). 3D-printed supercapacitor-powered electrochemiluminescent protein immunoarray. Biosens Bioelectron, 77, 188-93. Abstract Only.

Kaluzny, J., Purta, P., Poskin, Z., Rogers, J. D., Fawzi, A. A. (2016). Ex Vivo Confocal Spectroscopy of Autofluorescence in Age-Related Macular Degeneration. PLoS One, 11(9), e0162869. doi:10.1371/journal.pone.0162869.

Kim, Y.H., et al. (2015). A 3D human neural cell culture system for modeling Alzheimer's disease. Nat Protoc, 10(7), 985-1006.

Lavik, E. B., Klassen, H., Warfvinge, K., Langer, R., Young, M. J. (2005). Fabrication of degradable polymer scaffolds to direct the integration and differentiation of retinal progenitors. Biomaterials, 26(16), 3187-3196. doi:10.1016/j.biomaterials.2004.08.022.

Leach, J., Bivens, K., Collins, C., Schmidt, C. (2004). Development of photocrosslinkable hyaluronic acid-polyethylene glycol-peptide composite hydrogels for soft tissue engineering. Journal of Biomedical Materials Research Part A, 70(1), 74-82. doi:10.1002/jbm.a30063. Abstract Only.

Li, Q., Ford, M. C., Lavik, E. B., Madri, J. A. (2006). Modeling the neurovascular niche: VEGF- and BDNF-mediated cross-talk between neural stem cells and endothelial cells: an in vitro study. J Neurosci Res, 84(8), 1656-1668. doi:10.1002/jnr.21087. Abstract Only.

Lozano, R., Stevens, L., Thompson, B. C., Gilmore, K. J., Gorkin, R., 3rd, Stewart, E. M., Wallace, G. G. (2015). 3D printing of layered brain-like structures using peptide modified gellan gum substrates. Biomaterials, 67, 264-273. doi:10.1016/j.biomaterials.2015.07.022.

Madl, C.M., Katz, L.M., Heilshorn, S.C. (2016). Bio-Orthogonally Crosslinked, Engineered Protein Hydrogels with Tunable Mechanics and Biochemistry for Cell Encapsulation. Adv Funct Mater, 26(21), 3612-3620.

Maeda, E., et al., (2014). Significant increase in Young's modulus of ATDC5 cells during chondrogenic differentiation induced by PAMPS/PDMAAm double-network gel: comparison with induction by insulin. J Biomech, 47(13), 3408-14.

Meyer-Franke, A., Kaplan, M. R., Pfrieger, F. W., Barres, B. A. (1995). Characterization of the signaling interactions that promote the survival and growth of developing retinal ganglion cells in culture. Neuron, 15(4), 805-819.

Nah, J. W., Yu, L., Han, S. 0., Ahn, C. H., Kim, S. W. (2002). Artery wall binding peptide-poly(ethylene glycol)-grafted-poly(L-lysine)-based gene delivery to artery wall cells. J Control Release, 78(1-3), 273-284.

Peng, Q., Pei, K., Han, B., Li, R., Zhou, G., Liu, J. M., Gao, J. (2016). Inexpensive transparent nanoelectrode for crystalline silicon solar cells. Nanoscale Res Lett, 11(1), 312. doi:10.1186/s11671-016-1533-3.

Rauch, M. F., Michaud, M., Xu, H., Madri, J. A., Lavik, E. B. (2008). Co-culture of primary neural progenitor and endothelial cells in a macroporous gel promotes stable vascular networks in vivo. J Biomater Sci Polym Ed, 19(11), 1469-1485. doi:10.1163/156856208786140409.

Rosales, A.M., et al., (2015). Photoresponsive elastic properties of azobenzene-containing poly(ethylene-glycol)-based hydrogels. Biomacromolecules, 16(3), 798-806.

Royce Hynes, S., McGregor, L. M., Ford Rauch, M., Lavik, E. B. (2007). Photopolymerized poly(ethylene glycol)/poly (L-lysine) hydrogels for the delivery of neural progenitor cells. J Biomater Sci Polym Ed, 18(8), 1017-1030. doi:10.1163/156856207781494368.

Sarkar, S., et al. (2008). Fabrication of a layered microstructured polycaprolactone construct for 3-D tissue engineering. J Biomater Sci Polym Ed, 19(10), 1347-62.

Schaefer, K. A., Toral, M. A., Velez, G., Cox, A.I., Baker, S. A., Borcherding, N. C., Mahajan, V. B. (2016). Calpain-5 Expression in the Retina Localizes to Photoreceptor Synapses. Invest Ophthalmol Vis Sci, 57(6), 2509-2521. doi:10.1167/iovs.15-18680.

Schweiger, P.J., Jensen, K.B. (2016). Modeling human disease using organotypic cultures. Curr Opin Cell Biol, 43, 22-29.

Shadforth, A. M., Suzuki, S., Theodoropoulos, C., Richardson, N. A., Chirila, T. V., Harkin, D. G. (2015). A Bruch's membrane substitute fabricated from silk fibroin supports the function of retinal pigment epithelial cells in vitro. J Tissue Eng Regen Med. doi:10.1002/term.2089. Abstract Only.

Sicherer, S.H., Sampson, H.A. (2014). Food allergy: Epidemiology, pathogenesis, diagnosis, and treatment. J Allergy Clin Immunol, 133(2), 291-307.

Siegel, R.L., Miller, K.D., Jemal, A. (2016). Cancer statistics, 2016. CA Cancer J Clin, 66(1), 7-30.

Srinivasan, B., et al. (2015). TEER measurement techniques for in vitro barrier model systems. J Lab Autom, 20(2), 107-26.

Stett, A., Egert, U., Guenther, E., Hofmann, F., Meyer, T., Nisch, W., Haemmerle, H. (2003). Biological application of microelectrode arrays in drug discovery and basic research. Anal Bioanal Chem, 377(3), 486-495. doi:10.1007/s00216-003-2149-x.

Suikkola, J., Bjorninen, T., Mosallaei, M., Kankkunen, T., Iso-Ketola, P., Ukkonen, L., Mantysalo, M. (2016). Screen-Printing Fabrication and Characterization of Stretchable Electronics. Sci Rep, 6, 25784. doi:10.1038/srep25784.

Tunesi, M., et al. (2016). Optimization of a 3D Dynamic Culturing System for In Vitro Modeling of Frontotemporal Neurodegeneration-Relevant Pathologic Features. Front Aging Neurosci, 8, 146.

Williams, C., Rauch, M. F., Michaud, M., Robinson, R., Xu, H., Madri, J., Lavik, E. (2012). Short term interactions with long term consequences: modulation of chimeric vessels by neural progenitors. PLoS One, 7(12), e53208. doi:10.1371/journal.pone.0053208.

Wufsus, A.R., et al., (2015). Elastic behavior and platelet retraction in low- and high-density fibrin gels. Biophys J, 2015. 108(1), 173-83.

(56) References Cited

OTHER PUBLICATIONS

Yan, Y., et al. (2018). Derivation of Cortical Spheroids from Human Induced Pluripotent Stem Cells in a Suspension Bioreactor. Tissue Eng Part A. doi: 10.1089/ten.TEA.2016.0400. Abstract Only.

Yue, Z., Liu, X., Coates, P. T., & Wallace, G. G. (2016). Advances in printing biomaterials and living cells: implications for islet cell transplantation. Curr Opin Organ Transplant, 21(5), 467-475. doi:10.1097/mot.0000000000000346.

Zhou, W., Stukel, J. M., Cebull, H. L., Willits, R. K. (2016). Tuning the Mechanical Properties of Poly(Ethylene Glycol) Microgel-Based Scaffolds to Increase 3D Schwann Cell Proliferation. Macromol Biosci, 16(4), 535-544. doi:10.1002/mabi.201500336.

Zhao, Changwen, et al.; "Hierarchical PEG-Based 3D Patterns Grafting from Polymer Substrate by Surface Initiated Visible Light Photolithography," Supporting Information for Macromol. Rapid Commun., DOI: 10.1002/marc.201600307, 2016.

Zustiak, S. P., Leach, J. B. (2010). Hydrolytically degradable polyethylene glycol) hydrogel scaffolds with tunable degradation and mechanical properties. Biomacromolecules, 11(5), 1348-1357. doi:10.1021/bm100137q.

Zustiak S. P., Durbal, R., Leach, J.B. (2010). Influence of cell-adhesive peptide ligands on poly(ethylene glycol) hydrogel physical, mechanical and transport properties. Acta Biomater, 6(9), p. 3404-14.

Mazerik, J. N., et al., 3-D retina organoids: Building platforms for therapies of the future, Cell Medicine, vol. 10: 1-6; doi:101177/2155179018773758.

https://research.umbc.edu/umbc-research-news/?id=71946.

https://nei.nih.gov/ideation-winner.

https://www.challenge.com/challenge/nei-3-d-retina-organoid-challenge-3-d-roc/.

https://www.nih.gov/news-events/news-releases/national-eye-institute-awards-prize-retina-dish-competition.

Hynes, S. R., Rauch, M. F., Bertram, J. P., Lavik, E. B. (2009). A library of tunable poly(ethylene glycol)/poly(L-lysine) hydrogels to investigate the material cues that influence neural stem cell differentiation. J Biomed Mater Res A, 89(2), 499-509. doi:10.1002/jbm.a.31987.; Abstract Only.

Jung, J. P., Bhuiyan, D. B., & Ogle, B. M. (2016). Solid organ fabrication: comparison of decellularization to 3D bioprinting. Biomater Res, 20(1), 27. doi:10.1186/s40824-016-0074-2.

Li, Q., Ford, M. C., Lavik, E. B., Madri, J. A. (2006). Modeling the neurovascular niche: VEGF- and BDNF-mediated cross-talk between neural stem cells and endothelial cells: an in vitro study. J Neurosci Res, 84(8), 1656-1668. doi:10.1002/jnr.21087.

* cited by examiner

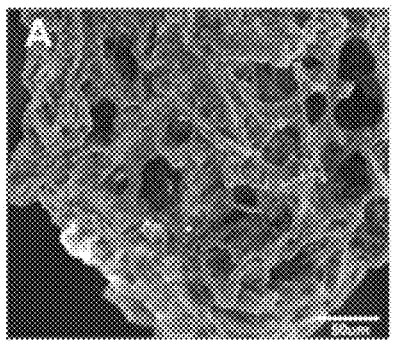
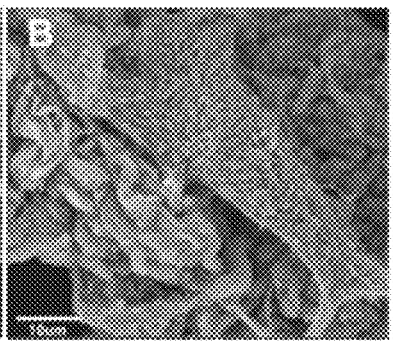
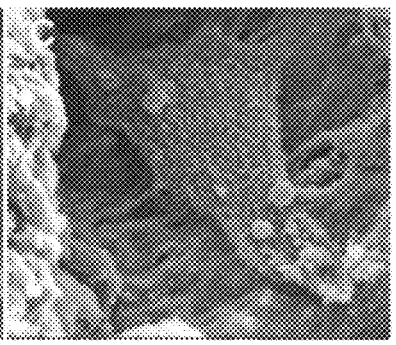
FIGURE 4A  FIGURE 4B  FIGURE 4C
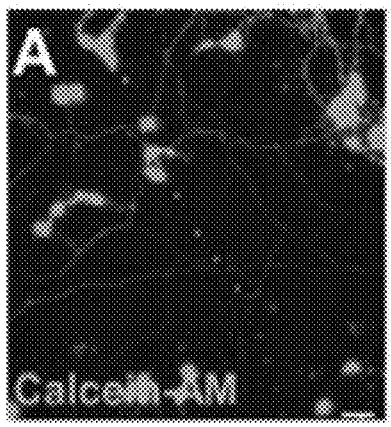
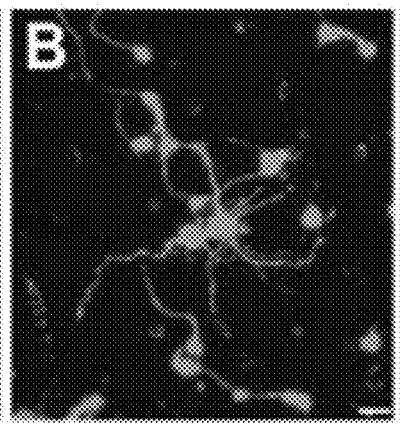
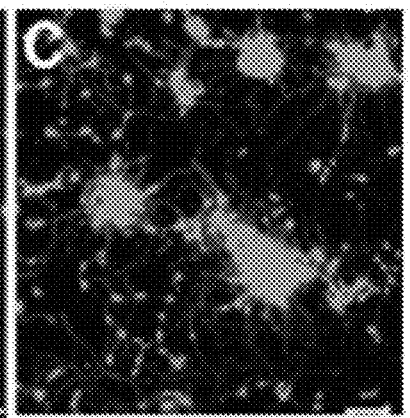
FIGURE 5A  FIGURE 5B  FIGURE 5C
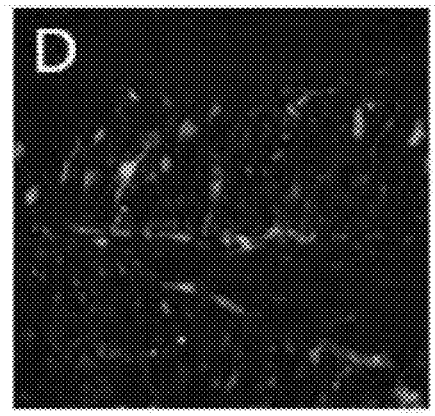
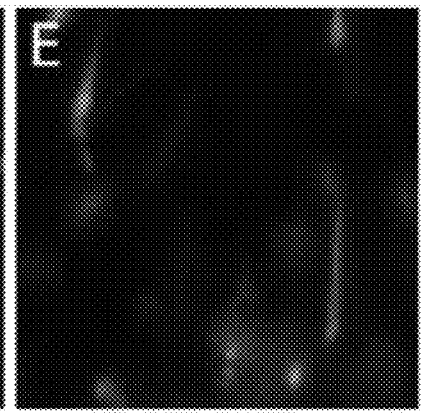
FIGURE 5D  FIGURE 5E

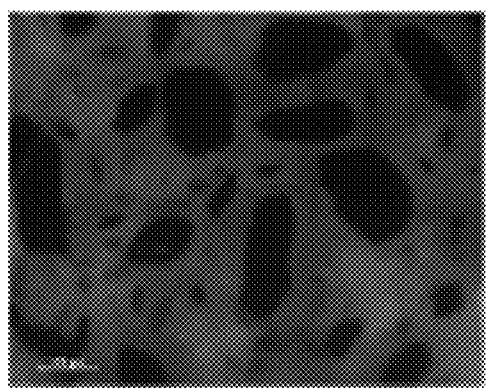
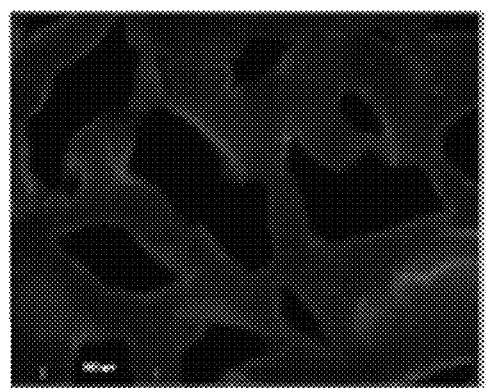
FIGURE 6A                FIGURE 6B
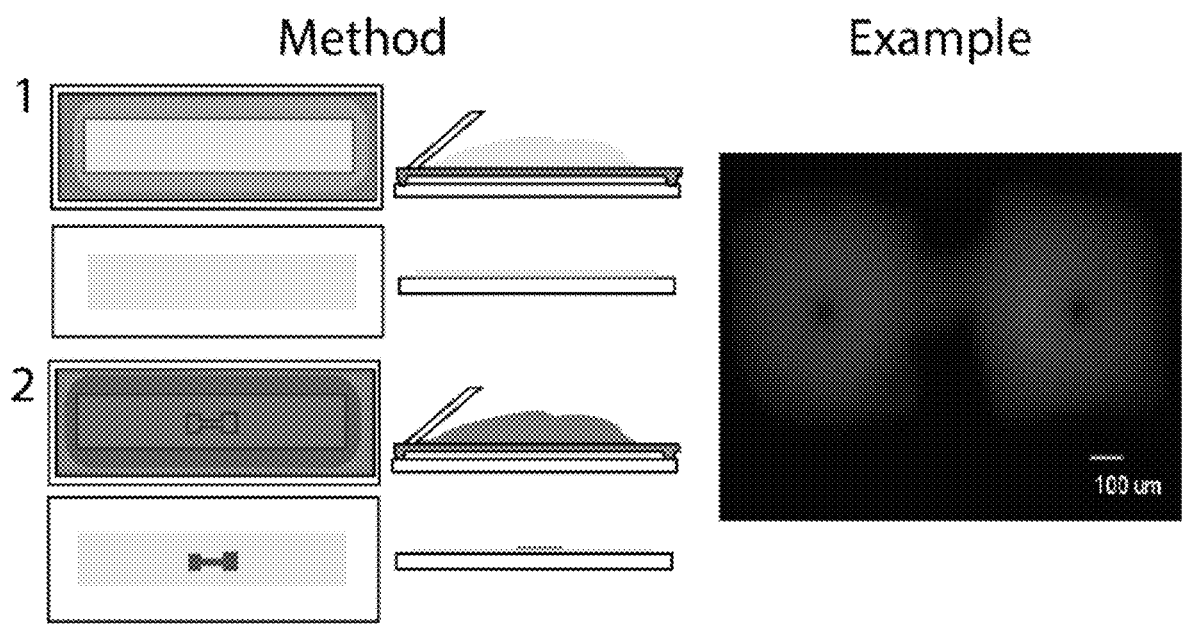
FIGURE 7

SCREEN PRINTING TISSUE MODELS

CROSS REFERENCE TO RELATED APPLICATIONS

This application is filed under the provisions of 35 U.S.C. § 111(a) and claims priority to U.S. Provisional Patent Application No. 62/599,977 filed on Dec. 18, 2017 in the name of Erin Lavik et al. and entitled "Screen Printing Tissue," which is hereby incorporated by reference herein in its entirety.

FIELD

The present invention relates to a process of simply, cheaply, and reproducibly creating complex tissue models using screen printing and the tissue model prepared using said screen printing process. These models are amenable to high throughput screening. They will allow the study of components of disease progression and can be used for screening therapies. Being able to efficiently model tissues for high throughput screening will allow for the investigation of the complex interactions between the cells and structures involved, and, ultimately, will provide a platform for investigating the interplay between the tissue and the microbiome. Further, the process and tissue models can be used for implantable therapies.

BACKGROUND OF THE INVENTION

High-throughput screening methods amenable to three dimensional cultures opens the possibility of efficiently investigating disease models and therapeutic interventions. However, the ability to build three dimensional models for these high-throughput systems has been primarily based on 3D printing, photolithography, and bioprinting. Each allows one to develop patterns and architectures that are seen in vivo, but they require materials and processes that are not always compatible with cells and progenitors, for example the shearing forces associated with many of the 3D printing technologies and UV light for the photopolymerizable approaches.

3D printing offers an exciting approach to facilitate organizing the cell types into models, for example, retinal models, but it is not without limitations particularly in relation to stem cells and retinal cells. Bioprinting allows printing of cells and hydrogels into complex architectures (Jung et al., 2016; Yue et al., 2016), which advantageously allows one to develop the kinds of patterns and architectures that are seen in vivo, but disadvantageously requires extruding the materials and cells through fine openings with high shear, as well as specialized equipment. While the cost of bioprinters has come down, the extrusion process requires bioinks that are compatible with the shearing associated with the approach as well as materials that protect cells during this process (Dubbin et al., 2016).

There is a continued need to develop new approaches to make in vitro complex tissue models that are simple, reproducible, cost effective, and avoid the extrusion issues associated with bioprinting and the UV light source in photolithography.

SUMMARY OF THE INVENTION

The present invention relates to a process of screen printing multilamellar structures that promote specific cellular organization and the tissue model obtained using said process. These models are amenable to high throughput screening and they will allow the study of components of disease progression and have the potential to be used for screening therapies.

In one aspect, a synthetic multilamellar tissue model is described, said model comprising (i) a substrate, (ii) a foundation comprising at least one layer comprising a hydrogel, and (iii) at least one non-foundational layer comprising one or more of proteins, cells, a hydrogel, a second constituent, collagen, and any combination thereof, wherein the synthetic multilamellar tissue model comprises at least one pattern having resolution in a range from about 20 µm to about 500 µm.

In another aspect, a process of making a multilamellar tissue model is described, said process comprising:
(a) positioning a first screen having an exposed first pattern over a substrate;
(b) placing a first solution to be printed onto the first screen, wherein the first solution comprises a hydrogel and optionally a second constituent;
(c) pushing a blade across the first screen to spread the first solution into the exposed first pattern;
(d) removing the first screen to reveal a first layer comprising the hydrogel and optionally the second constituent;
(e) positioning a second screen having an exposed second pattern over the first layer;
(f) placing a second solution to be printed onto the second screen, wherein the second solution comprises one or more of proteins, cells, additional hydrogel, a second constituent, collagen, gelatin, and any combination thereof;
(g) pushing a blade across the second screen to spread the second solution into the exposed second pattern; and
(h) removing the second screen to reveal a second layer positioned on the first layer comprising the hydrogel,
wherein the process does not require exposure to of the layers UV light, bioinks, or shearing processes.

In yet another aspect, a synthetic multilamellar tissue model produced using the process described herein is disclosed.

In still another aspect, a three-dimensional tissue model is described, said model comprising (a) the multilamellar tissue model of claim 1, and (b) layers positioned using bioprinting, photolithography, and/or 3D printing.

Other aspects, features and embodiments of the invention will be more fully apparent from the ensuing disclosure and appended claims.

BRIEF DESCRIPTION OF THE FIGURES

FIG. 4A is a scanning electron micrograph of decellularized ON. The cells express microvillae and are SOX2(+)/GFAP(+)/Chx10(+) at this stage.

FIG. 4B is a scanning electron micrograph of human ON-aNPCs extending on an ON-laminar surface.

FIG. 4C is another scanning electron micrograph of human ON-aNPCs extending on an ON-laminar surface.

FIG. 5A is an image of the growth of Retinal Ganglion Cells (RGCs) in PLL-based gels. RGCs cells migrate into hydrogels and readily extend elaborate neurites in three dimensions. RGCs were seeded onto hydrogels and stained using calcein-AM (green) to label cell somas and neurites. Live confocal z-stack images were acquired. The RGCs retained their stereotyped morphology.

FIG. 5B is an image of the growth of Amacrine Cells (ACs) in PLL-based gels. ACs cells migrate into hydrogels and readily extend elaborate neurites in three dimensions. ACs were seeded onto hydrogels and stained using calcein-AM (green) to label cell somas and neurites. Live confocal z-stack images were acquired. The ACs retained their stereotyped morphology.

FIG. 5C is an image of the growth of Retinal Ganglion Cells (RGCs) and Amacrine Cells (ACs) in PLL-based gels. RGCs and ACs were seeded onto hydrogels and stained using calcein-AM (green) to label cell somas and neurites. Live confocal z-stack images were acquired. The coculture of RGCs and ACs retained their stereotyped morphology.

FIG. 5D is an image of retinal progenitor cells oriented in the polarized fashion in response to being in polymer scaffolds (Lavik et al., 2005).

FIG. 5E is an image of retinal progenitor cells oriented in the polarized fashion in response to being in PLGA scaffolds (Lavik et al., 2005). The cells follow architectural cues, and in doing so, they take on morphologies that are consistent with retinal cells.

FIG. 6A is an image of a PLL-based gel labeled with FITC, which reacts with the charged free amines on lysine.

FIG. 6B is an image of anti-fibronectin immunostaining of PLL-based gel reacted with fibronectin. The fibronectin absorbs to the charged amines on the gels.

FIG. 7 is an illustration and image of a dye-loaded hydrogel printed on a hydrogel layer. The barbell structure is at the limits of the resolution available with a 100 μm mesh screen.

DETAILED DESCRIPTION, AND PREFERRED EMBODIMENTS THEREOF

Figure 1:
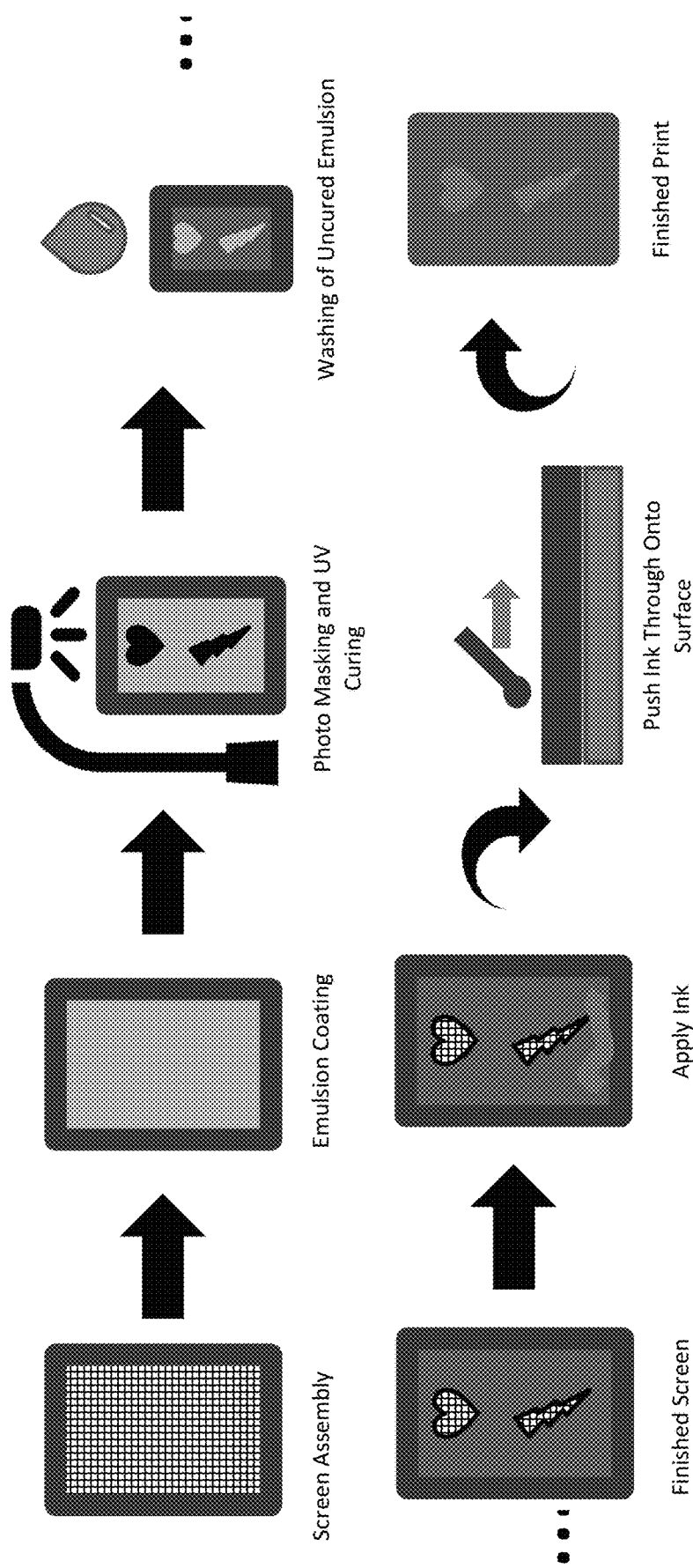
FIG. 1 is a schematic of the process of screen printing.

The present invention relates to a complex tissue model and a process of making same, said process using screen printing, which avoids the disadvantages associated with UV light, bioinks, and shearing described hereinabove. The process is simple, reproducible, and highly scalable, making the tissue model suitable for high-throughput assays. Using screen printing, a range of gels and cells can be printed in multiple layers and in complex patterns with high resolution and reproducibility. Preferably, the complex tissue model mimics a tissue that is multilamellar in nature.

The changes in the extracellular matrix, particularly associated with Bruch's membrane, play a significant role in the pathology of diseases including age-related macular degeneration (AMD) but the methods to investigate this have been limited up until now (Al Gwairi et al., 2016; Booij et al., 2010; Hollyfield et al., 2008). By patterning a Bruch's membrane structure and then building a retinal model, a healthy retina with tight retinal pigment epithelium (RPE) junctions can be modeled as well as the diseased retina with the degenerating RPE layer. By coupling this approach with human RPE cells and human adult neural stem cells derived from the eye and optic nerve, which have been shown to express markers for the major retinal cell types, a tissue system can be produced that models the 3D retina and optic nerve structures in a scalable and reproducible manner that is exceptionally well suited to high-throughput screening approaches for understanding and treating diseases of the retina. The process described herein allows for the recapitulation of the layers of the retina and provides the matrix cues to promote the critical polarization of the cell types and promote the formation of appropriate synapses in the system, as well as the enhanced survival of target neurons.

The usefulness of the presently described tissue model and process of producing same is not limited to the modeling of retinal tissue. Neurodegenerative diseases are one of the greatest health burdens of this century, and yet the disease models are lacking (Schweiger et al., 2016, Tunesi et al., 2016, Choi et al. 2014). The critical cell types associated with neural models are particularly fragile, and viability can be poor when they experience shear, especially through extrusion systems (Kim et al., 2015, Gu et al., 2016). Thus, most work has focused on printing materials to which the cells are added separately (Lozano et al., 2015) or the use of gels to reduce the shear experienced by neural cells (Madl et al., 2015). Screen printing represents an alternative that reduces the shearing and, based on our preliminary experiments, leads to robust survival of even extremely sensitive human iPS (induced pluripotent stem) cells.

In addition, the prevalence of food allergies are growing with approximately 7% of children and 6% of adults being diagnosed with one or more food allergies including celiac disease (Sicherer et al., 2014). Beyond these conditions, diseases of the colon include irritable bowel syndrome (IBS), a poorly understood but highly pervasive condition affecting approximately 11% of the population around the world (Canavan et al., 2014), and colon cancer. Approximately 4.4% of the population will be diagnosed with colon cancer in their lifetimes (Siegel et al., 2016). We need better models to understand these conditions and to screen for therapies. Prior art in vitro intestinal models are intriguing systems but are not ideal for high throughput screening and transport analysis due to their enclosed lumen limiting access to apical cell surfaces. Advantageously, the intestine is well suited to screen printing. The tissue is multilamellar, but to be functional, the cells must be organized appropriately. The resolution of the critical architecture in the colon, the crypt, is 80-100 um in diameter (Araki et al., 1995) which is well within the range for screen printing described herein. One of the most critical assays for the intestine is testing of the barrier function of the cultured cells, which is typically accomplished by employing transepithelial electrical resistance (TEER) measurement (Srinivasan et al., 2015). We can build the electrodes required for TEER measurement into the screen-printed system using standard electrical screen printing techniques that are biologically compatible (Kadimisetty et al., 2016).

Taking a cue from the electronics industry (Peng et al., 2016; Suikkola et al., 2016), the process described herein uses screen printing to develop highly scalable hydrogel-cell tissue models. Screen printing offers several advantages including, but not limited to, (1) modeling tissue comprising many types of materials and cells including those that are sensitive to UV light and extrusion, (2) the materials and cells can be patterned within a wide range of three-dimensional, multilamellar structures, (3) by varying the screen structure, layers can be created across a wide range of thicknesses, and (4) these models can be built quickly and at low cost. For example, a new tissue can be built within a day with screening materials for about $1 USD per finished pattern.

An example of the screen printing process is shown in FIG. 1. In screen printing, an emulsion is applied to a screen and exposed to light to cure the emulsion. Printed transparencies having a pattern thereon are then used as a mask to expose portions of the emulsion to UV light, followed by the removal of the unexposed areas, i.e., the pattern. The prepared screen is then positioned over a surface (e.g., the substrate), solutions comprising gel precursors, cells, and/or other layer components are added to the screen, and a blade is used to move the solutions over the screen to the removed pattern. Following removal of the screen, the pattern can be seen on the surface. For the biological screen printing described herein, preferably the screens have pores in a range from about 20 µm to about 500 µm, more preferably about 80 µm to about 500 µm. Other preferable resolutions include, but are not limited to, about 80 µm to about 250 µm, about 80 µm to about 200 µm, about 80 µm to about 150 µm, about 80 µm to about 120 µm, or about 250 µm to about 500 µm. It should be appreciated that the screen for each new layer may have the same pore size of, or a different pore size from, the screen used for the previous layer, as readily determined by the person skilled in the art. In other words, each new layer may have the same resolution, or a different resolution, from the previous layer. Preferably, the screen pore size chosen provides for maximum reproducibility and resolution and does not compromise the layer components, e.g., a substantial amount of undifferentiated cells survive post-printing. For the purposes of this application, a "substantial amount of undifferentiated cells" corresponds to preferably greater than 60%, more preferably greater than 70%, and even more preferably greater than 80% of the cells survive the screening process without differentiation and without the presence of a matrix which augments survival.

As defined herein, the "substrate" can be any material that is inert to the gels and/or cells printed thereon and can be sterilized including, but not limited to, glass, stainless steel, metals, ceramics, plastics, gas-permeable membranes such as a silicone (polydimethylsiloxane) membrane, and other polysiloxanes, fabric, degradable polymer films or membranes, other polymer membranes, electrospun materials, and any combination thereof. For the purposes of the present disclosure, reference will be made to the substrate being a glass slide but it should be understood that it is not limited as such.

As defined herein, a "layer" corresponds to a material that is printed and that has a thickness that is substantially consistent over a surface, for example a surface that is substantially planar. It should be appreciated that because of the nature of screen printing, a layer could have cavities, vias, holes, or some pattern therein having a different chemical and/or biological makeup than the rest of the layer.

As defined herein, "substantially devoid" corresponds to the presence of less than 1 ppm, preferably less than 1 ppb, even more preferably less than 1 ppt of the particular material referred to.

As a foundation for the described process, hydrogels based on poly(ethylene glycol) (PEG) can be synthesized, wherein the hydrogels gel via vinylsulfone-thiol chemistry in 3-5 minutes (Jeong et al., 2014). In one embodiment, a hydrogel comprising PEG and polylysine (PLL) is synthesized, wherein the PLL-based gels are made by functionalizing the PLL-PEG macromers with vinylsulfone and reacting with PEG-thiol macromers to make the gels. By tuning the ratio of PEG with polylysine a wide range of moduli can be achieved (Hynes et al., 2009; Zustiak et al., 2010). For example, by choosing the ratio of the two components and the molecular weight, the elasticity of the resulting gels can be controlled (Hynes et al., 2009, Zustiak & Leach, 2010, Zustiak et al., 2010, Royce Hynes et al., 2007). Other hydrogel foundations are contemplated herein including, but not limited to, poly(ethylene glycol) coupled with at least one second constituent such as PLL, hyaluronic acid (HA), poly-γ-(glutamic acid) (γ-PGA), poly(aspartic acid) (PAA), and/or poly(arginine). Another hydrogel foundation comprises gelatin, with or without one or both of PEG or a second constituent. It should be appreciated by the person skilled in the art that any hydrogel material that gels in about 3-10 minutes can be used as the hydrogel foundation, wherein the choice is generally dependent on the cell type and the tissue being modeled. HA-based gels can be made in a similar manner to the PLL-based ones with macromers of HA functionalized with PEG-thiol groups combined with PEG-vinylsulfone macromers to make the hydrogels (Jeong et al., 2014). The presence of the second constituent, e.g., PLL, enables the absorption of proteins of interest into the gels, considerably reducing time and cost compared to using each protein as a basis for the gel (Hynes et al., 2009).

As defined herein, the "foundation" is the hydrogel-containing layer or layers that is printed onto the substrate and serves as the platform for the tissue model. The foundation supports the survival, organization, and maturation of the cells in this model system. By screen printing the hydrogel-containing layer or layers, i.e., the foundation, the physical guidance cues can be provided through the cell permissive regions and non cell-permissive regions as well as through the chemical guidance cues provided by the absorption of extracellular matrix molecules. Non cell-permissive regions can be made using a hydrogel consisting of or consisting essentially of PEG. For example, the screen printed hydrogel foundation can have architectural cues comprising columns of a PEG-polylysine matrix in a non cell-permissive matrix consisting of or consisting essentially of PEG. The foundation can comprise one, two, three, four, five, six, seven, eight, nine, or ten or more layers, wherein each layer can be the same as or different from one another. Optionally, at least one layer of the foundation can comprise at least one protein or at least one cell, as readily understood by the person skilled in the art.

As introduced hereinabove, the presence of the second constituent, e.g., PLL, enables the absorption or reaction of proteins of interest to the gels. For example, FIG. 6A shows the PEG-PLL gel with absorbed fibronectin and FIG. 6B shows the PEG-PLL gel with absorbed rhodamine-antifibronectin antibody. The extracellular matrix proteins absorb or react with to the charged polylysine backbone of the gels. The absorption process is rapid and stable and the proteins do not release from the gel over weeks (Hynes et al., 2009). In contrast, no proteins absorb to hydrogels consisting of or consisting essentially of PEG, i.e., non cell-permissive portions, which will impede cell attachment (Leach et al., 2004).

In practice, the screen having the specific pattern thereon is placed over the substrate, a solution comprising the components to be printed in the specific layers are combined, mixed together and placed over the substrate, and then a blade is pushed across the screen to ensure that the solution is evenly spread over the screen. The pattern is dependent on the layer being printed, as readily determined by the person skilled in the art. The hydrogel components to be printed are present at the appropriate concentration, for example in a range from about 1% to about 20%, more preferably about 10% in solution, at the appropriate pH, for example, physiological pH, wherein the concentration and pH are dependent on the material and the mechanics desired since the mechanics of the resulting gel impact cell behavior. The solutions are preferably aqueous and can include at least one of physiologically appropriate buffers, salts, sugars, water, and other physiologically appropriate species including, but not limited to, proteins and drugs. A protein of interest can be absorbed to or reacted with the secondary constituent before printing the macromer, or the protein of interest can be printed on the gel in a separate step. The latter is appropriate when the cellular components interact with the surface. The positioning of the protein within the gel (i.e., absorbed to or reacted with the secondary constituent) or on the gel is dependent on the resolution to be obtained, the effect on the robustness of lamination between layers, and the desired extent of interaction of the cellular components with the surface.

The thickness of each layer printed using the process described herein will be a function of the distance the screen is placed from the substrate or last layer printed, as readily determined by the person skilled in the art. The thickness of each layer can be in a range from about 5 µm to about 5 mm, depending on the desired tissue model. Spacers such as Mylar film (from 5 µm-400 µm) can optionally be used to set the distance for one or more layers. Mylar is advantageous since it can be autoclaved and disposed of after printing to avoid contamination. The thickness of each layer can be confirmed using any number of techniques including, but not limited to, ellipsometry, atomic force microscopy (AFM), and scanning electron microscopy (SEM). Ellipsometry is suitable for thicknesses less than 50 rpm. For greater thicknesses, SEM and AFM preferred.

Because the process described herein uses vinylsulfone-thiol chemistry, the lamination between the gel layers is robust. The extent of lamination, or lack thereof, can be characterized using protocols previously developed in our laboratory involving a pull test (Sarkar et al., 2008) as well as the parallel plate rheometry for the laminated structures versus bulk material. In the event that the layers are not properly laminated, a chemical bonding layer utilizing some of the amines in the hydrogel can be added (Id.).

The desired elastic modulus is dependent on the cells comprised therein. For example, preferably the hydrogels have an elastic modulus for neural cells in a range from about 1000-8000 Pa, preferably in a range from about 3500-6000 Pa, for neural cell migration and orientation in and on the hydrogel. Fibrin-containing gels preferably have a modulus in a range from about 100-10000 Pa (Wufsus et al., 2015). Gels comprising valvular interstitial cells preferably have a modulus in a range from about 100-6000 Pa (Rosales et al., 2015). Gels comprising the chondrogenic cell line, ATDC5, preferably have a modulus in a range from about 100-500 Pa, preferably about 150-250 Pa (Maeda et al., 2014). Gels comprising human mesenchymal stem cells preferably have a modulus in a range from about 15 to about 75 Pa (Li et al., 2014). Gels comprising Schwann cells preferably have a modulus in a range from about 4 to about 12 kPa (Gu et al., 2012). Both the gelation time and the mechanical properties of each layer can be determined using a parallel plate rheometer.

The gel components are synthesized and preferably filtered prior to printing, e.g., through 0.45 µm filters, e.g., TEFLON™ filters. The solutions comprising the respective components to be printed are also preferably exposed to UV light in a tissue culture hood as a second sterilization step. The screens, blades, and all the other materials used in the process can be autoclaved.

Once the foundation is prepared, one or more non-foundational layers are positioned thereon to complete the tissue model, wherein the non-foundational layers comprise one or more of proteins, cells, (e.g., epithelial cells, goblet cells, dendritic cells, neural cells, RPE cells, photoreceptor cells, bipolar cells, amacrine cells, horizontal cells), additional hydrogel as described herein, a hydrogel comprising a second constituent as described herein, collagen, gelatin, drugs, and any combination thereof. The non-foundational layers can be positioned using the screen printing process described herein, or by culturing, by stamping, and/or by absorption. For example, a solution comprising the components of the specific non-foundational layer can be introduced to a screen for printing. The solutions are preferably aqueous and comprise the components of the specific non-foundational layer can include at least one of physiologically appropriate buffers, salts, sugars, water, serum, and other physiologically appropriate species including, but not limited to, proteins and drugs. It should be appreciated that there can be one, two, three, four, five, six, seven, eight, nine, or ten or more non-foundational layers, wherein each non-foundational layer can be the same as or different from each other non-foundational layer, as readily understood by the person skilled in the art.

Accordingly, in a first aspect, a synthetic multilamellar tissue model is described, said model comprising (i) a substrate, (ii) a foundation comprising at least one layer comprising a hydrogel, and (iii) at least one non-foundational layer comprising one or more of proteins, cells, a hydrogel, a second constituent, collagen, and any combination thereof, wherein the synthetic multilamellar tissue model comprises at least one pattern having resolution in a range from about 20 µm to about 500 µm. Advantageously, the hydrogel sets without using UV radiation and the foundation and non-foundational layer are both substantially devoid of bioinks. Further, when the non-foundational layer comprises cells, greater than 60%, preferably greater than 70%, and more preferably greater than 80% of the cells survive the screening process without differentiation and without the presence of a matrix which augments survival.

In a second aspect, a process of making a multilamellar tissue model is described, said process comprising:
(a) positioning a first screen having an exposed first pattern over a substrate;
(b) placing a first solution to be printed onto the first screen, wherein the first solution comprises a hydrogel and optionally a second constituent;
(c) pushing a blade across the first screen to spread the first solution into the exposed first pattern; (d) removing the first screen to reveal a first layer comprising the hydrogel and optionally the second constituent;
(e) positioning a second screen having an exposed second pattern over the first layer;
(f) placing a second solution to be printed onto the second screen, wherein the second solution comprises one or more of proteins, cells, additional hydrogel, a second constituent, collagen, gelatin, and any combination thereof;
(g) pushing a blade across the second screen to spread the second solution into the exposed second pattern; and
(h) removing the second screen to reveal a second layer positioned on the first layer comprising the hydrogel, wherein the process does not require exposure to of the layers UV light, bioinks, or shearing processes. Additional layers can be layered in succession by positioning an nth screen having an exposed nth pattern over the n−1 layer; placing an nth solution to be printed on the nth screen, wherein the nth solution comprises one or more of proteins, cells, additional hydrogel, a second constituent, collagen, gelatin, and any combination thereof; pushing a blade across the nth screen to spread the nth solution into the exposed nth pattern; and removing the nth screen to reveal an nth layer positioned on the n−1 layer, wherein n=3, 4, 5, 6, 7, 8, 9, 10, or greater.

The appropriate foundation is important to successfully direct the cells into the appropriate cell types and structures. For example, referring to FIG. 5, the present inventors have used the PEG-polylysine hydrogel system either on its own or in the presence of laminin to support the organization and differentiation of a range of cell types from neural stem cells (Hynes et al., 2009; Royce et al., 2007) and endothelial cells in vascular networks (Ford et al., 2006; Li et al., 2006; Rauch et al., 2008; Williams et al., 2012) to retinal progenitors (Hynes et al., 2010; Lavik et al., 2005), retinal ganglion cells, and amacrine cells (Hertz et al., 2013).

The screen printing process increases the survival of cells, particularly those which are sensitive to shear forces and UV-light, by eliminating the shearing associated with more traditional 3D printing, using materials that gel without UV exposure, or using bioinks. The open matrices lead to robust proliferation and organization of cells, for example neural or retinal cells. The approach and the materials provided are exceptional for building multilamellar structures, e.g., of the retina or colon, and providing the extracellular matrix cues and support to foster healthy cells and tissue organization. Preferably, greater than 60%, more preferably greater than 70%, and even more preferably greater than 80% of the cells survive the screening process without differentiation and without the presence of a matrix which augments survival, e.g., a PEG-based bioink.

One of the major attractions of the process described herein is the ability to screen print structures for high throughput screening. Advantageously, 96 or 384 replicates can be printed on a single plate in minutes, making this an extremely efficient method for building up tissue models quickly as well as printing patterns for multiple tissue models at the same time. Since printing into small wells is relatively challenging, layer(s) suitable for imaging can be printed on a substrate followed by the adherence of PDMS wells or polystyrene colony rings thereto to create isolated wells.

The tissue model can further comprise a multichannel electrode array system for electroretinography (ERG) measurements or the electrodes required for TEER measurement can be patterned into the screen-printed model using standard electrical screen printing techniques that are biologically compatible. The positioning of the electrodes on the tissue model will be readily understood by the person skilled in the art.

Advantageously, with the screen printing approach described herein, it is possible to print a layer of cells which will achieve the necessary guidance to polarize appropriately, when necessary. For example, channels of cell permissive matrix such as laminin-absorbed hydrogel surrounded by non cell-permissive matrix such as a pure PEG gel serve to orient the cells being printed. By patterning the cell-permissive protein gels with non cell-permissive gels, interfaces can be created that guide the cell types to polarize in the matrix. The use of the appropriate patterns to polarize cells can be readily determined by the person skilled in the art.

The screen printing process described herein allows one to build up patterned, multilamellar systems cheaply and easily with high resolution. All of the materials are readily available and autoclavable including the hydrogel components since they are not hydrolytically degradable. Screen printing allows one to make many replicates in a single printing process that preserves the viability of the cellular components and provides the critical extracellular matrix cues to build retinal structures in three dimensions.

Advantageously, screen printing can complement other methods including bioprinting to make three-dimensional tissue models. Having multiple approaches to make tissue models will help to build on the breakthroughs with iPS cells and high throughput screening to understand disease and develop treatments. Accordingly, in another aspect of the invention, a tissue model comprises (a) multilamellar screen printed layers prepared using the process of screen printing described herein, wherein greater than 60%, more preferably greater than 70%, and even more preferably greater than 80% of the cells in the screen printed tissue model survive the screen printing process without differentiation and without the presence of a matrix which augments survival, and (b) layers positioned using bioprinting, photolithography, and/or 3D printing. For example, the "substrate" could be an article that was prepared using bioprinting, photolithography, and/or 3D printing, wherein layers are screen printed thereon, as described herein.

The features and advantages of the invention are more fully illustrated by the following non-limiting examples, wherein all parts and percentages are by weight, unless otherwise expressly stated.

Example 1

Human Optic Nerve Neural Progenitor Cells

Figure 2:
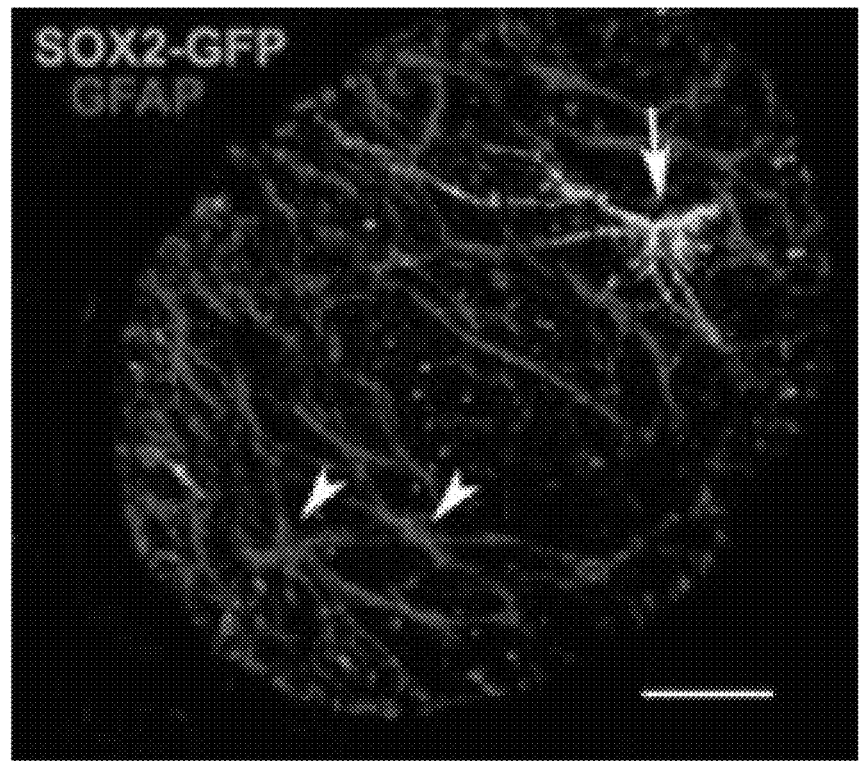
FIG. 2 is an image of SOX2-GFAP(+)ON-aNPCS expressed in a double mutant (ER2-SOX2-Cre X Td-Tomato-LoxP(GFP) animal). Both GFP(+)/GFAP(+) aNPCs and GFAP(+) astrocytes are seen.
Figures 3A, 3B:
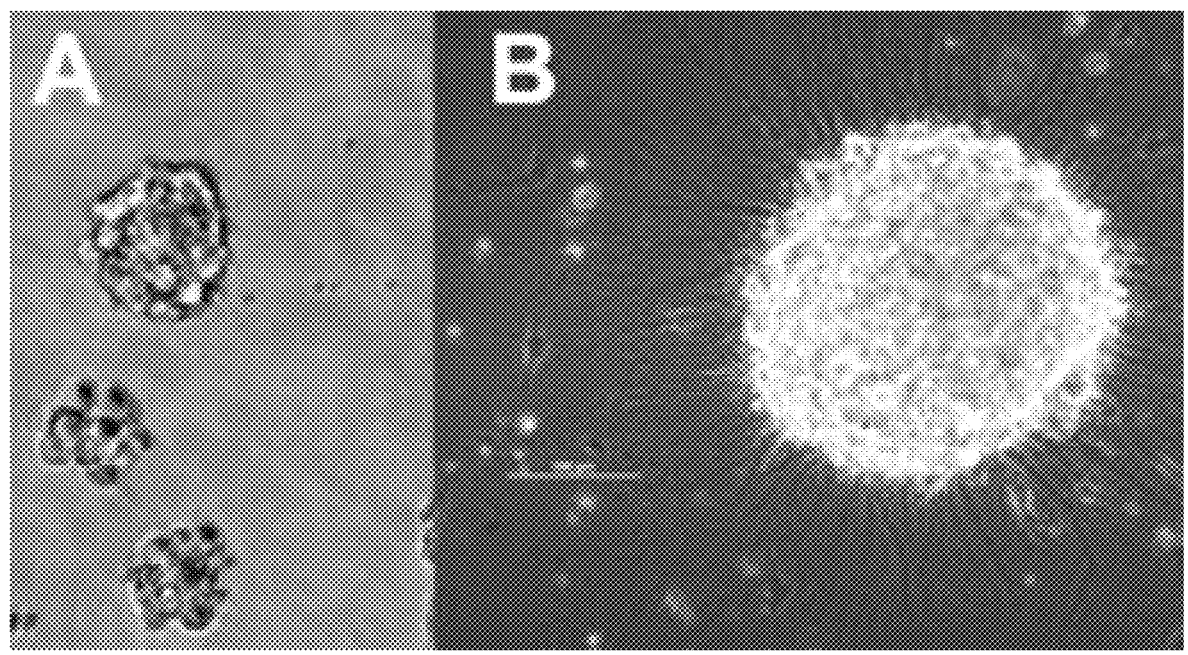
FIG. 3A is an image of early aNPC neurospheres grown from rodent ON. Scale bar: 50 um.
FIG. 3B is an image of aNPC neurospheres grown from rodent ON that were subsequently grown on a laminin coated plate. Scale bar: 100 uM.

We have isolated adult neural progenitor cells (aNPCs) from young and mature optic nerve. These cells are SOX2 (+)/Nestin(+)/GFAP(+) (FIG. 2), and can be distinguished from their surroundings by: 1) their ability to be cultured continuously for >10 replications, 2) their ability to give rise to astrocytes, oligodendrocytes and rarely, neurons, 3) their ability to form neurospheres (FIGS. 3A and B), and 4) their age-associated depletability. These cells are maintained in a high concentration matrix medium. Withdrawal of growth medium and replacement with fetal bovine serum results in differentiation into largely glial cells. Our data suggests that these cells are used during optic nerve (ON) growth in adulthood, to maintain gliogenesis in high stress areas. Loss of these cells results in segmental hypomyelination and ON hypoplasia.

Following aNPC growth and subculture, these cells can be grown on decellularized ON matrices (FIG. 4A). The human cells grown on these matrices then "stretch out," assuming a shape and expression more typical of cells in vivo (FIGS. 4B and 4C).

The hydrogel screen printing process will allow us to build and identify the most appropriate artificially constructed extracellular matrix. By using an adult neural progenitor cell (aNPC)-artificial matrix construct, in conjunction with a retinal ganglion cell (RGC)-survival assay, we can determine the optimum conditions for aNPC survival, autologous growth factor expression, and RGC-axonal development, all critical conditions required for normal eye development and growth.

Structure of the Retinal Model
Hydrogel Facilitates Retinal Cell Differential and Organization The screen printing process avoids the bioprinting shearing aspect which allows a far broader range of materials and gels to be used. The major requirement for screen printing is that the gel be able to set up, crosslink, or phase separate within seconds to a minute, preferably in a range from about 10 seconds to about 10 minutes, more preferably in a range from about 30 seconds to about 5 minutes, without the use of UV light. This is readily achievable with a range of coupling chemistries. We focus on the vinylsulfone-thiol chemistry because it is easily performed and highly biocompatible, avoiding light or toxic coupling agents (Jin et al., 2010; Nah et al., 2002; Zhou et al., 2016).

Polarization of the Cells in the Layers

With the screen printing approach it is possible to print a layer of cells which will achieve the necessary guidance to polarize appropriately. For example, vertical channels of permissive matrix such as laminin-absorbed hydrogel surrounded by non cell-permissive matrix such as a pure PEG gel that resists protein absorption and provides structural guidance cues to orient the cells can be printed. By patterning the cell-permissive protein gels with non cell-permissive gels, we are able to create interfaces that will act as architecture to guide the retinal cell types to polarize in the matrix.

Resolution of Features and Reproducibility

The resolution of features in the printing process is dictated primarily by the resolution of the screens. The 110 mesh screen has pores on the order of 130 µm. A 200 mesh screen has pores on the order of 74 pun. In the electronics industry, resolution down to 20 µm is common (Hyun et al., 2015), but about 100 µm is more than adequate for printing of the tissue models for the purposes of this experiment. Finer meshes can lead to finer resolution features, however, a resolution of about 100 µm is more than adequate to achieve the polarized orientations in the retina.

Screen Printing Cells

We have tested meshes with 100 micron pores to determine the viability of cells post printing. We have used iPS cells differentiated down a neural lineage from a colleague. It was determined that 84+/−2.6% of the cells are viable post-printing in the absence of any survival-augmenting matrix (Lozano et al., 2015).

Protocol for Screen Printing the Retinal Model for High-Throughput Screening
Preparing the Cells Cells are obtained from human donor optic nerves and eyes for which we have obtained using an UMB IRB exemption, and are currently available in the lab. These cells are grown and stored as low-subculture passage cultures, and express appropriate markers (Chx10, MBP, GFAP, SOX2, NeuN). Following replating of the subcultures, they are subsequently dissociated with elastase and placed in the appropriate fluid. Retinal cells are prepared using triturated retinae digested with Papain. Retinal ganglion cells (RGCs) and amacrine cells are isolated following removal of microglia using Thy-1 immuno-linked beads (Miltenyi) (Barres et al., 1988; Meyer-Franke et al., 1995).

Photoreceptors are isolated in a similar manner from the Thy-1(−) eluate, but utilizing the appropriate surface markers for photoreceptors (glycosylphosphatidylinositol (GPO)-anchored cell surface molecule ecto-5'-nucleotidase (CD73) for rods). The purified populations (>65%) are then employed in the preparation of cell printing. The RGCs are also utilized for co-incubation with the aNPC surface assays. These assays are prepared in triplicate, and are compared against both commercially available artificial matrices, as well as laminin-coated surfaces.

Preparing the Screens

The mask for the screen is printed on an inkjet printer on a transparency. The screens are coated with the emulsion, the transparency is applied, and the screen is exposed to a UV light source followed by rinsing to remove uncrosslinked emulsion. The screens are then autoclaved and ready for use. Using these standard materials traditionally used for screen printing t-shirts, we can obtain reproducible features on the order of 100 µm.

Choice of Support Structure for the Retina: Glass Coverslips Versus Oxygen Transport Membrane One can print on a range of substrates including glass coverslips and gas-permeable membranes such as a silicone (polydimethylsiloxane) membrane. For the purposes of the experiments herein, we focus on coverslips and glass plates because of the ease with which they can facilitate multiwell culture and high-throughput screening. It is understood that the appropriate substrate is not limited to glass plates and coverslips and is readily determined by the person skilled in the art.

Printing Bruch's and ON Membrane Surfaces

Figure 8:
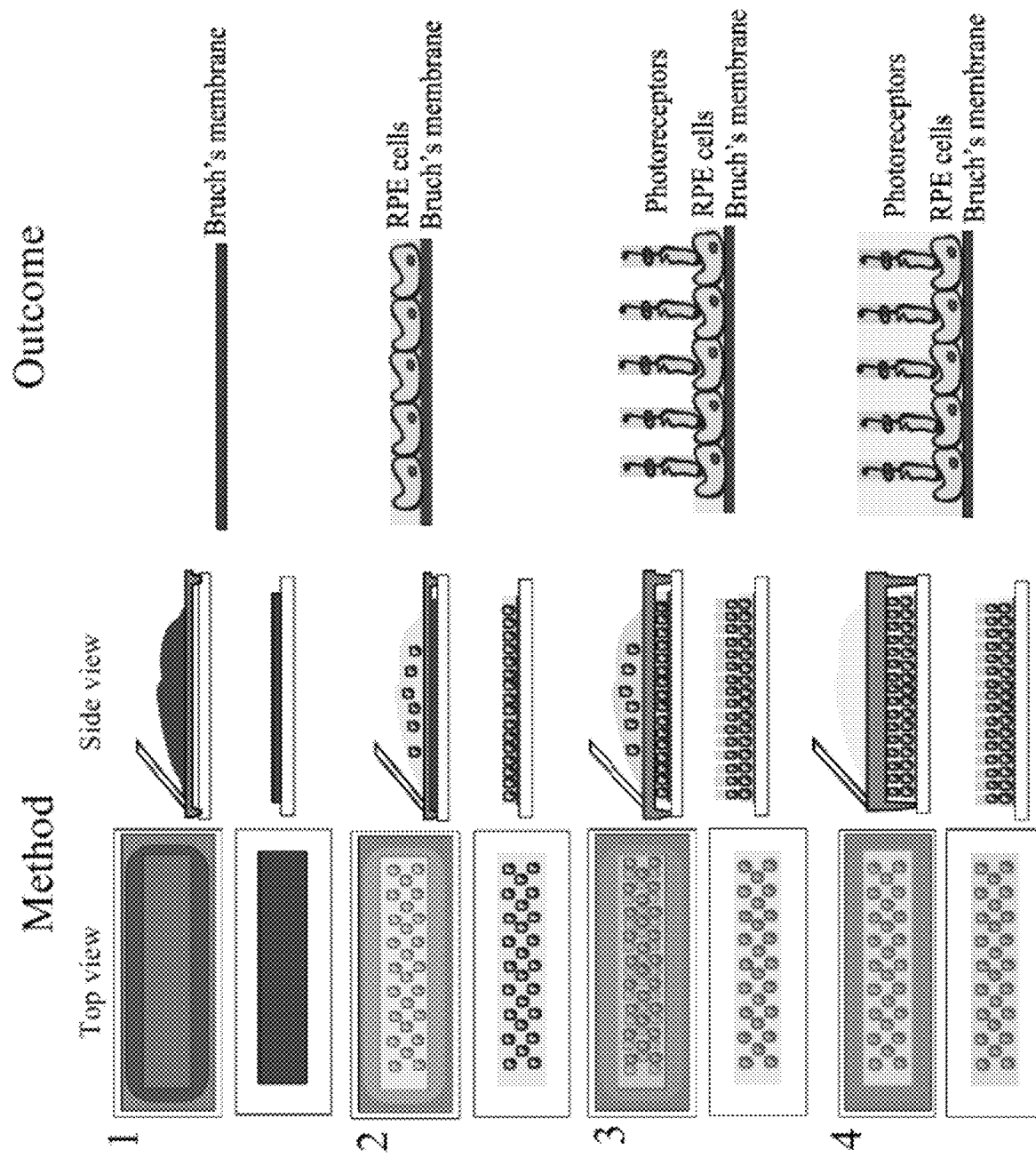
FIG. 8 is a schematic of the screen printing process for printing Bruch's membrane and two of the cellular layers of a retinal tissue model. In this schematic, the green gel is cell-permissive, and the yellow is the non cell-permissive PEG-based gel.

A membrane layer that interfaces with the RPE layer consists of laminin, fibronectin, collagen type VI, and glycosaminoglycans (Booij et al., 2010). A cocktail of these molecules can be printed on the foundational polylysine-PEG printed gel as a model for the healthy Bruch's membrane and ON surfaces. Alterations to the chemistry of these different surfaces can be investigated. A schematic for screen printing a retinal model is shown in FIG. 8.

Printing RPE and ON aNPCs

Human RPE and aNPCs cells can be printed on a laminin-coated matrix. The printed models can be characterized a number of ways including, but not limited to, looking at cell survival (live/dead assay), the formation of tight junctions (BESTI; ZO-1) (Brandl et al., 2014; Shadforth et al., 2015), the expression of RPE- and mature glial specific markers (RPE65), MBP, CNPase, Glut-1 (Ahmado et al., 2011), and the response to variations in Bruch's membrane layer.

Printing Photoreceptors in the Matrix

The photoreceptor progenitors can be printed in the laminin-coated matrix. Marker expression as well as phagocytosis of the outer segments by the RPE cells can be assessed.

Printing Bipolar, Horizontal, and Amacrine Cells

Different masks can be used to pattern the horizontal, bipolar, and amacrine cells, when present. The bipolar cells can be aligned with the photoreceptors. The horizontal and amacrine cells will be offset.

Ganglion cells, when present, can be aligned with the bipolar cells in the laminin-coated matrix.

Culturing the Constructs

The materials completely set within 3 minutes. At that point, the constructs are immersed in the appropriate media and cultured at 37° C. with media changes twice per week or as needed.

Characterizing the Structures

The constructs are characterized structurally as described below immunohistochemically using epifluorescent microscopy, confocal microscopy, and a high throughput imager, the acumen cellista. The acumen cellista uses laser scanning technology using three lasers (blue, green, CyS) to quantitatively assess fluorescent signals. While it can create images with a resolution equivalent to 200×, the strength of the system is that it can perform a rapid quantification of multiple fluorescent signals through several millimeters of tissue. This will allow us to not only rapidly image many structures but to also quantify the fluorescence and, therefore, the number of cells and their marker expression using immunocytochemistry without having to section the constructs. Synapses in the system will be characterized using an antibody for PSD95 (Schaefer et al., 2016).

Assessing Functionality

One of the attractions of the screen printing process is that it can be used on a range of surfaces. To assess function, the retinal and ON structures can be printed on multichannel electrode array systems to do the equivalent of ERG in a dish. This can be coupled with validation by mimicking aspects of diseases, including alterations in Bruch's membrane that are associated with AMD. In addition, the response from different structures in response to light exposure can be screened using an LED-based stimulation system (Stett et al., 2003).

Calcification of the elastin layer, crosslinking of the collagen layers, and overall thickening have been associated with a reduction in elasticity that may play a role in AMD progression (Femandez-Godino et al., 2016; Kaluzny et al., 2016). Increases in glycosaminoglycans may also play a role in disease (Booij et al., 2010; Fernandez-Godino et al., 2016; Kaluzny et al., 2016). With the PEG-polylysine system as the support, these molecules can be varied and the cellular response of the RPE and retinal cells determined.

2-Aminophosphonobutyric acid (AP4), is a blocker of the on-signal pathway in the retina. Advantageously, using the multielectrode array system, the B-wave amplitude before, during and after wash out of the drug can be measured. The B-wave is primarily due to Muller cell and bipolar cell activity (Stett et al., 2003).

Example 2

With mesh sizes of 100 μm, we obtained the cross piece pattern shown in FIG. 7, having a finest feature of 90 μm wide. The "barbell" of FIG. 7 has been designed to promote neural synapses between cell populations in the narrow region between two cell populations in the square areas.

Meshes with 100 micron or 250 micron pores were also tested to determine the viability of cells post printing. Since neural-driven iPS cells tend to die or differentiate in response to shear (Faulkner-Jones et al., 2015, Yan et al., 2017), they provide the most robust way to demonstrate the limits on the screen printing technology. Using iPS cells differentiated down a neural linage from a colleague, 84+/−2.6% and 93+/−3.5% of the cells were viable post-printing in the absence of any matrix which typically augments survival for the 100 micron and the 250 micron pores, respectively (Lozano et al., 2015). Cell survival was assessed using the trypan blue exclusion assay. While finer mesh sizes do impact survival, both are significantly higher than survival percentages seen with traditional 3D printers in the absence of bioink. Accordingly, this approach is extremely well suited to building retinal and other tissue structures.

Example 3

Figure 9:
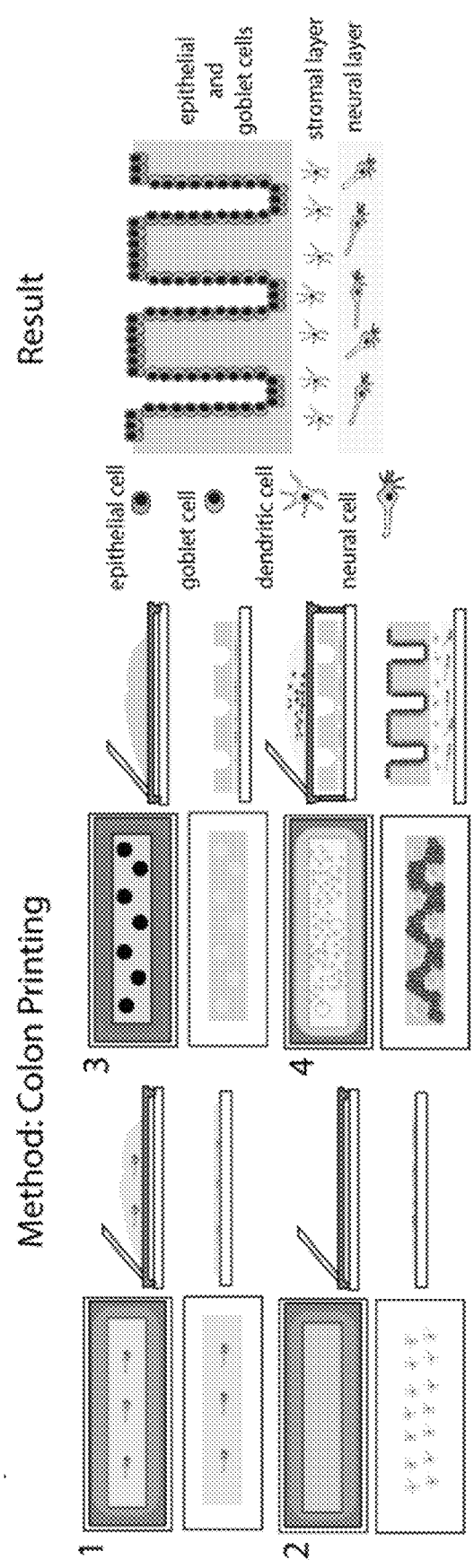
FIG. 9 is a schematic of the screen printing process for printing a colon model.

An example of a screen printed colon is illustrated in FIG. 9. The screen printed colon comprises a neural layer, stromal layer with dendritic cells, and the epithelial/goblet cell layer with the crypt structures that are critical to normal cell function. The crypts will be printed by printing gels with holes that are the appropriate dimensions (approximately 200-300 μm) and then printing the epithelial and goblet cell layers.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art, based on the disclosure herein. The invention therefore is to be broadly construed, as encompassing all such variations, modifications and alternative embodiments within the spirit and scope of the claims hereafter set forth.

REFERENCES

Ahmado, A., Carr, A. J., Vugler, A. A., Semo, M., Gias, C., Lawrence, J. M., Coffey, P. J. (2011). Induction of differentiation by pyruvate and DMEM in the human retinal pigment epithelium cell line ARPE-19. *Invest Ophthalmol Vis Sci.* 52(10), 7148-7159. doi: 10.1167/iovs. 10-6374.

Al Gwairi, O., Thach, L., Zheng, W., Osman, N., Little, P. J. (2016). Cellular and Molecular Pathology of Age-Related Macular Degeneration: Potential Role for Proteoglycans. *J Ophthalmol.* doi:10.1155/2016/2913612.

Araki, K., Ogata, T. (1995). Three-dimensional configuration of crypts of different types of colorectal adenomas. *Scanning Microsc,* 9(1): 149-56.

Barres, B. A., Silverstein, B. E., Corey, D. P., Chun, L. L. (1988). Immunological, morphological, and electrophysiological variation among retinal ganglion cells purified by panning. *Neuron.* 1(9), 791-803.

Booij, J. C., Baas, D. C., Beisekeeva, J., Gorge's, T. G., Bergen, A. A. (2010). The dynamic nature of Bruch's membrane. *Prog Retin Eye Res.* 29(1), 1-18. doi: 10.1016/j.preteyeres.2009.08.003.

Brandl, C., Zimmermann, S. J., Milenkovic, V. M., Rosendahl, S. M., Grassmann, F., Milenkovic, A., Weber, B. H. (2014). In-depth characterisation of Retinal Pigment Epithelium (RPE) cells derived from human induced pluripotent stem cells (hiPSC). *Neuromolecular Med.* 16(3), 551-564. doi: 10.1007/s12017-014-8308-8.

Canavan, C., West, J., Card, T. (2014). The epidemiology of irritable bowel syndrome. *Clin Epidemiol,* 6, 71-80.

Choi, S. H., et al. (2014). A three-dimensional human neural cell culture model of Alzheimer's disease. *Nature,* 515 (7526), 274-8.

Dubbin, K., Hori, Y., Lewis, K. K., Heilshorn, S. C. (2016). Dual-Stage Crosslinking of a Gel-Phase Bioink Improves Cell Viability and Homogeneity for 3D Bioprinting. *Adv Healthc Mater. doi:* 10.1002/adhm.201600636.

Faulkner-Jones, A., et al. (2015). Bioprinting of human pluripotent stem cells and their directed differentiation into hepatocyte-like cells for the generation of mini-livers in 3D. *Biofabrication,* 7(4), 044102.

Fernandez-Godino, R., Pierce, E. A., Garland, D. L. (2016). Extracellular Matrix Alterations and Deposit Formation in AMD. *Adv Exp Med Biol.* 854, 53-58. doi: 10.1007/978-3-319-17121-0_8.

Ford, M. C., Bertram, J. P., Hynes, S. R., Michaud, M., Li, Q., Young, M., Lavik, E. B. (2006). A macroporous hydrogel for the coculture of neural progenitor and endothelial cells to form functional vascular networks in vivo. *Proc Natl Acad Sci USA.* 103(8), 2512-2517. doi: 10.1073/pnas.0506020102.

Gu, Q., et al. (2016). Stem Cell Bioprinting: Functional 3D Neural Mini-Tissues from Printed Gel-Based Bioink and Human Neural Stem Cells. *Adv Healthcare Mater,* 5(12), p. 1428.

Gu, Y., et al., (2012). The influence of substrate stiffness on the behavior and functions of Schwann cells in culture. *Biomaterials,* 33(28), 6672-81.

Hertz, J., Robinson, R., Valenzuela, D. A., Lavik, E. B., Goldberg, J. L. (2013). A tunable synthetic hydrogel system for culture of retinal ganglion cells and amacrine cells. *Acta Biomater.* 9(8). 7622-7629. doi:10.1016/j.actbio.2013.04.048.

Hollyfield, J. G., Bonilha, V. L., Raybom, M. E., Yang, X., Shadrach, K. G., Lu, L., Perez, V. L. (2008). Oxidative damage-induced inflammation initiates age-related macular degeneration. *Nat Med.* 14(2), 194-198.

Hynes, S. R., Lavik, E. B. (2010). A tissue-engineered approach towards retinal repair: scaffolds for cell transplantation to the subretinal space. *Graefes Arch Clin Exp Ophthalmol.* 248(6). 763-778. doi:10.1007/s00417-009-1263-7.

Hynes, S. R., Rauch, M. F., Bertram, J. P., Lavik, E. B. (2009). A library of tunable poly(ethylene glycol)/poly(L-lysine) hydrogels to investigate the material cues that influence neural stem cell differentiation. *J Biomed Mater Res A.* 89(2). 499-509. doi: 10.1002/jbm.a.31987.

Hyun, W. J., Lim, S., Ahn, B. Y., Lewis, J. A., Frisbie, C. D., Francis, L. F. (2015). Screen Printing of Highly Loaded Silver Inks on Plastic Substrates Using Silicon Stencils. *ACS Appl Mater Interfaces.* 7(23), 12619-12624. doi: 10.1021/acsami.5b02487.

Jeong, C. G., et al. (2014). Screening of hyaluronic acid-poly(ethylene glycol) composite hydrogels to support intervertebral disc cell biosynthesis using artificial neural network analysis. *Acta Biomater,* 10(8): 3421-30.

Jin, R., Moreira Teixeira, L. S., Krouwels, A., Dijkstra, P. J., van Blitterswijk, C. A., Karperien, M., Feijen, J. (2010). Synthesis and characterization of hyaluronic acid-poly (ethylene glycol) hydrogels via Michael addition: An injectable biomaterial for cartilage repair. *Acta Biomater.* 6(6), 1968-1977. doi: 10.1016/j.actbio.2009.12.024.

Jung, J. P., Bhuiyan, D. B., & Ogle, B. M. (2016). Solid organ fabrication: comparison of decellularization to 3D bioprinting. *Biomater Res.* 20(1). 27. doi: 10.1186/s40824-016-0074-2.

Kadimisetty, K., et al. (2016). 3D-printed supercapacitor-powered electrochemiluminescent protein immunoarray. *Biosens Bioelectron,* 77, 188-93.

Kaluzny, J., Purta, P., Poskin, Z., Rogers, J. D., Fawzi, A. A. (2016). Ex Vivo Confocal Spectroscopy of Autofluorescence in Age-Related Macular Degeneration. *PLoS One.* 11(9), e0162869. doi:10.1371/journal.pone.0162869

Kim, Y. H., et al. (2015). A 3D human neural cell culture system for modeling Alzheimer's disease. *Nat Protoc,* 10(7), 985-1006.

Lavik, E. B., Klassen, H., Warfvinge, K., Langer, R., Young, M. J. (2005). Fabrication of degradable polymer scaffolds to direct the integration and differentiation of retinal progenitors. *Biomaterials.* 26(16), 3187-3196. doi: 10.1016/j.biomaterials.2004.08.022.

Leach, J., Bivens, K., Collins, C., Schmidt, C. (2004). Development of photocrosslinkable hyaluronic acid-polyethylene glycol-peptide composite hydrogels for soft tissue engineering. *Journal of Biomedical Materials Research Part A.* 70(1), 74-82. doi: 10.1002/jbm.a.30063.

Li, Q., Ford, M. C., Lavik, E. B., Madri, J. A. (2006). Modeling the neurovascular niche: VEGF- and BDNF-mediated cross-talk between neural stem cells and endothelial cells: an in vitro study. *J Neurosci Res.* 84(8). 1656-1668. doi: 10.1002/jnr.21087.

Li, Z., et al., (2012). High-efficiency matrix modulus-induced cardiac differentiation of human mesenchymal stem cells inside a thermosensitive hydrogel. *Acta Biomater,* 8(10), 3586-95.

Lozano, R., Stevens, L., Thompson, B. C., Gilmore, K. J., Gorkin, R, 3rd, Stewart, E. M., Wallace, G. G. (2015). 3D printing of layered brain-like structures using peptide modified gellan gum substrates. *Biomaterials.* 67, 264-273. doi: 10.1016/j.biomaterials.2015.07.022.

Madl, C. M., Katz, L. M., Heilshorn, S. C. (2016). Bio-Orthogonally Crosslinked, Engineered Protein Hydrogels with Tunable Mechanics and Biochemistry for Cell Encapsulation. *Adv Funct Mater,* 26(21), 3612-3620.

Maeda, E., et al., (2014). Significant increase in Young's modulus of ATDC5 cells during chondrogenic differentiation induced by PAMPS/PDMAAm double-network gel: comparison with induction by insulin. *J Biomech,* 47(13), 3408-14.

Meyer-Franke, A., Kaplan, M. R., Pfrieger, F. W., Barres, B. A. (1995). Characterization of the signaling interactions that promote the survival and growth of developing retinal ganglion cells in culture. *Neuron.* 15(4). 805-819.

Nah, J. W., Yu, L., Han, S. O., Ahn, C. H., Kim, S. W. (2002). Artery wall binding peptide-poly(ethylene glycol)-grafted-poly(L-lysine)-based gene delivery to artery wall cells. *J Control Release.* 78(1-3), 273-284.

Peng, Q., Pei, K., Han, B., Li, R., Zhou, G., Liu, J. M., Gao, J. (2016). Inexpensive transparent nanoelectrode for crystalline silicon solar cells. *Nanoscale Res Lett.* 11(1). 312. doi:10.1186/s11671-016-1533-3.

Rauch, M. F., Michaud, M., Xu, H., Madri, J. A., Lavik, E. B. (2008). Co-culture of primary neural progenitor and endothelial cells in a macroporous gel promotes stable vascular networks in vivo. *J Biomater Sci Polym Ed.* 19(11), 1469-1485. doi: 10.1163/156856208786140409.

Rosales, A. M., et al., (2015). Photoresponsive elastic properties of azobenzene-containing poly(ethylene-glycol)-based hydrogels. *Biomacromolecules,* 16(3), 798-806.

Royce Hynes, S., McGregor, L. M., Ford Rauch, M., Lavik, E. B. (2007). Photopolymerized poly(ethylene glycol)/poly(L-lysine) hydrogels for the delivery of neural progenitor cells. *J Biomater Sci Polym Ed.* 18(8). 1017-1030. doi:10.1163/156856207781494368

Sarkar, S., et al. (2008). Fabrication of a layered microstructured polycaprolactone construct for 3-D tissue engineering. *J Biomater Sci Polym Ed,* 19(10), 1347-62.

Schaefer, K. A., Toral, M. A., Velez, G., Cox, A. I., Baker, S. A., Borcherding, N. C., Mahajan, V. B. (2016). Calpain-5 Expression in the Retina Localizes to Photoreceptor Synapses. *Invest Ophthalmol Vis Sci.* 57(6), 2509-2521. doi: 10.1167/iovs. 15-18680.

Schweiger, P. J., Jensen, K. B. (2016). Modeling human disease using organotypic cultures. *Curr Opin Cell Biol,* 43, 22-29.

Shadforth, A. M., Suzuki, S., Theodoropoulos, C., Richardson, N. A., Chirila, T. V., Harkin, D. G. (2015). A Bruch's membrane substitute fabricated from silk fibroin supports the function of retinal pigment epithelial cells in vitro. *J Tissue Eng Regen Med.* doi: 10.1002/term.2089.

Sicherer, S. H., Sampson, H. A. (2014). Food allergy: Epidemiology, pathogenesis, diagnosis, and treatment *J Allergy Clin Immunol,* 133(2), 291-307.

Siegel, R. L., Miller, K. D., Jemal, A. (2016). Cancer statistics, 2016. *CA Cancer J Clin,* 66(1), 7-30.

Srinivasan, B., et al. (2015). TEER measurement techniques for in vitro barrier model systems. *J Lab Autom*, 20(2), 107-26.

Stett, A., Egert, U., Guenther, E., Hofmann, F., Meyer, T., Nisch, W., Haemmerle, H. (2003). Biological application of microelectrode arrays in drug discovery and basic research. *Anal Bioanal Chem.* 377(3), 486-495. doi: 10.1007/s00216-003-2149-x.

Suikkola, J., Bjorninen, T., Mosallaei, M., Kankkunen, T., Iso-Ketola, P., Ukkonen, L., Mantysalo, M. (2016). Screen-Printing Fabrication and Characterization of Stretchable Electronics. *Sci Rep.* 6, 25784. doi: 10.1038/srep25784.

Tunesi, M., et al. (2016). Optimization of a 3D Dynamic Culturing System for In Vitro Modeling of Frontotemporal Neurodegeneration-Relevant Pathologic Features. *Front Aging Neurosci.* 8, 146.

Williams, C., Rauch, M. F., Michaud, M., Robinson, R., Xu, H., Madri, J., Lavik, E. (2012). Short term interactions with long term consequences: modulation of chimeric vessels by neural progenitors. *PLoS One.* 7(12), e53208. doi: 10.1371/journal.pone.0053208.

Wufsus, A. R., et al., (2015). Elastic behavior and platelet retraction in low- and high-density fibrin gels. *Biophys J,* 2015. 108(1), 173-83.

Yan, Y., et al. (2018). Derivation of Cortical Spheroids from Human Induced Pluripotent Stem Cells in a Suspension Bioreactor. *Tissue Eng Part A.* doi: 10.1089/ten.TEA.2016.0400.

Yue, Z., Liu, X., Coates, P. T., & Wallace, G. G. (2016). Advances in printing biomaterials and living cells: implications for islet cell transplantation. *Curr Opin Organ Transplant.* 21(5). 467-475. doi: 10.1097/mot.0000000000000346.

Zhou, W., Stukel, J. M., Cebull, H. L., Willits, R. K. (2016). Tuning the Mechanical Properties of Poly(Ethylene Glycol) Microgel-Based Scaffolds to Increase 3D Schwann Cell Proliferation. *Macromol Biosci.* 16(4), 535-544. doi: 10.1002/mabi.201500336.

Zustiak, S. P., Leach, J. B. (2010). Hydrolytically degradable polyethylene glycol) hydrogel scaffolds with tunable degradation and mechanical properties. *Biomacromolecules,* 11(5), 1348-1357. doi:10.1021/bm100137q.

Zustiak, S. P., Durbal, R., Leach, J. B. (2010). Influence of cell-adhesive peptide ligands on poly(ethylene glycol) hydrogel physical, mechanical and transport properties. *Acta Biomater,* 6(9), p. 3404-14.

What is claimed is:

1. A process of making a multilamellar tissue model, said process comprising:
    (a) positioning a first screen having an exposed first pattern over a substrate;
    (b) placing a first solution to be printed onto the first screen, wherein the first solution comprises a hydrogel and optionally an additional constituent;
    (c) pushing a blade across the first screen to spread the first solution into the exposed first pattern;
    (d) removing the first screen to reveal a first layer comprising the hydrogel and optionally the additional constituent;
    (e) positioning a second screen having an exposed second pattern over the first layer;
    (f) placing a second solution to be printed onto the second screen, wherein the second solution comprises one or more of a protein, a cell, additional hydrogel, additional hydrogel comprising an additional constituent, collagen, gelatin, and any combination thereof;
    (g) pushing a blade across the second screen to spread the second solution into the exposed second pattern; and
    (h) removing the second screen to reveal a second layer positioned on the first layer comprising the hydrogel, wherein the process does not require exposure of the layers to UV light, bioinks, or shearing processes.

2. The process of claim 1, wherein the multilamellar tissue model comprises (i) the substrate, (ii) the first layer comprising at least one layer comprising a hydrogel, and (iii) the second layer comprising one or more of a protein, a cell, additional hydrogel, additional hydrogel comprising an additional constituent, collagen, gelatin, and any combination thereof.

3. The process of claim 1, wherein the multilamellar tissue model further comprises at least one electrode patterned therein.

4. The process of claim 1, wherein the model comprises at least one cell-permissive portion and a non cell-permissive portion.

5. The process of claim 1, wherein the hydrogel comprises poly(ethylene glycol) (PEG), gelatin, or both.

6. The process of claim 5, wherein the hydrogel further comprises an additional constituent selected from the group consisting of polylysine (PLL), hyaluronic acid (HA), poly-γ-(glutamic acid) (γ-PGA), poly(aspartic acid) (PAA), poly (arginine), and any combination thereof.

7. The process of claim 6, wherein the additional constituent further comprises a protein that was absorbed to, or reacted with, the additional constituent.

8. The process of claim 1, wherein the substrate comprises a material selected from the group consisting of glass, stainless steel, metal, ceramic, plastic, gas-permeable membranes, polysiloxanes, fabric, degradable polymer films, degradable polymer membranes, electrospun materials, and any combination thereof.

9. The process of claim 1, wherein the solutions are aqueous and further comprise at least one component selected from the group consisting of physiologically appropriate buffers, salts, sugars, proteins and drugs.

10. The process of claim 1, wherein the second layer comprises cells and wherein greater than 60% of the cells survive the screening process without differentiation and without the presence of a matrix which augments survival.

11. The process of claim 1, wherein at least one pattern has a resolution in a range from about 20 μm to about 500 μm.

12. The process of claim 1, further comprising the printing of a third layer, said process comprising
    (i) positioning a third screen having an exposed third pattern over the second layer;
    (j) placing a third solution to be printed onto the third screen, wherein the third solution comprises one or more of proteins, cells, additional hydrogel, additional hydrogel comprising an additional constituent, collagen, gelatin, and any combination thereof;
    (k) pushing a blade across the third screen to spread the third solution into the exposed third pattern; and
    (l) removing the third screen to reveal a third layer positioned on the second layer.

13. The process of claim 12, further comprising printing a fourth layer, optionally a fifth layer, optionally a sixth layer, optionally a seventh layer, optionally an eighth layer, optionally a ninth layer, and optionally a tenth layer using a process analogous to the printing of any of the first, second, or third layers.

14. The process of claim 1, wherein hydrogel layers are able to set up, crosslink, or phase separate without exposure to light.

15. The process of claim 1, wherein hydrogel layers gel using vinylsulfone-thiol chemistry.

16. The process of claim 1, wherein the additional constituent is selected from the group consisting of polylysine (PLL), hyaluronic add (HA), poly-y-(glutamic add) (y-PGA), poly(aspartic add) (PAA), poly(arginine), and any combination thereof.

* * * * *